(12) United States Patent
Shenderova et al.

(10) Patent No.: US 6,866,678 B2
(45) Date of Patent: Mar. 15, 2005

(54) PHOTOTHERAPEUTIC TREATMENT METHODS AND APPARATUS

(75) Inventors: Olga Shenderova, Raleigh, NC (US); Gary E. McGuire, Chapel Hill, NC (US)

(73) Assignee: Interbational Technology Center, Raleigh, NC (US)

( * ) Notice: Subject to any disclaimer, the term of this patent is extended or adjusted under 35 U.S.C. 154(b) by 46 days.

(21) Appl. No.: 10/315,420

(22) Filed: Dec. 10, 2002

(65) Prior Publication Data

US 2004/0111132 A1 Jun. 10, 2004

(51) Int. Cl.$^7$ .............................................. A61N 5/06
(52) U.S. Cl. ....................................... 607/88; 128/898
(58) Field of Search ................... 128/898; 607/88–94; 313/502–506

(56) References Cited

U.S. PATENT DOCUMENTS

| | | | |
|---|---|---|---|
| 4,523,189 A | | 6/1985 | Takahara et al. |
| 4,552,782 A | | 11/1985 | Cattell et al. |
| 4,646,743 A | | 3/1987 | Parris |
| 4,672,969 A | | 6/1987 | Dew |
| 4,686,986 A | | 8/1987 | Fenyö et al. |
| 4,751,427 A | * | 6/1988 | Barrow et al. ............. 313/503 |
| 4,930,504 A | | 6/1990 | Diamantopoulos et al. |
| 4,975,691 A | * | 12/1990 | Lee ............................ 345/79 |
| 5,126,214 A | * | 6/1992 | Tokailin et al. ............ 428/690 |
| 5,131,065 A | * | 7/1992 | Briggs et al. ............... 385/120 |
| 5,179,316 A | | 1/1993 | Kellam |
| 5,445,146 A | | 8/1995 | Bellinger |
| 5,453,661 A | | 9/1995 | Auciello et al. |
| 5,556,612 A | | 9/1996 | Anderson et al. |
| 5,634,080 A | * | 5/1997 | Kikinis et al. ............... 710/73 |
| 5,660,461 A | | 8/1997 | Ignatius et al. |
| 5,712,528 A | * | 1/1998 | Barrow et al. .............. 313/506 |

(List continued on next page.)

OTHER PUBLICATIONS

Chen et al, Developments in Luminescence and Display Materials Over the Last 100 years as Reflected in Electrochemical Society Publications, Aug. 6, 2002, Journal of The Electrochemical Society.*

(List continued on next page.)

Primary Examiner—Roy D. Gibson
Assistant Examiner—Henry M Johnson, III
(74) Attorney, Agent, or Firm—Miller Patent Services; Jerry A. Miller

(57) ABSTRACT

A thin film electroluminescent (TFEL) phototherapy device based on high field electroluminescence (HFEL) or from organic light emitting devices (OLED), consistent with certain embodiments of the present invention has a battery and a charging circuit coupled to the battery, so that when connected to a source of current acts to charge the battery. A TFEL panel produces light when voltage from the power source (battery or AC source) is applied. A processor such as a microprocessor is used to control the application of voltage from the power source to the TFEL panel under control of a control program. A housing is used to contain the battery, the charging circuit and the processor and carry the TFEL panel on an outer surface thereof. In one embodiment, the housing incorporates a removable cover that uncovers a household electrical plug useful for supplying charging current to the charger. In use, a method of carrying out phototherapy, consistent with certain embodiments of the invention involves diagnosing a condition of an affected area of tissue that can be treated with phototherapy. A treatment protocol is determined including, for example, a treatment light intensity, a treatment time, a light modulation characteristic and a treatment light wavelength suitable for treating the condition. The affected area is then irradiated with light from the TFEL panel in accord with the treatment protocol.

58 Claims, 4 Drawing Sheets

U.S. PATENT DOCUMENTS

| | | | |
|---|---|---|---|
| 5,728,090 A | | 3/1998 | Martin et al. |
| 5,776,074 A | | 7/1998 | Marzorati |
| 5,778,894 A | | 7/1998 | Dorogi et al. |
| 5,786,797 A | * | 7/1998 | Kapoor et al. ............... 345/79 |
| 5,796,120 A | * | 8/1998 | Summers et al. ............. 257/30 |
| 5,869,350 A | | 2/1999 | Heeger et al. |
| 5,908,415 A | | 6/1999 | Sinofsky |
| 5,921,652 A | | 7/1999 | Parker et al. |
| 5,944,748 A | | 8/1999 | Mager et al. |
| 5,957,960 A | | 9/1999 | Chen et al. |
| 5,989,245 A | | 11/1999 | Prescott |
| 6,004,344 A | | 12/1999 | Fujii |
| 6,019,482 A | | 2/2000 | Everett |
| 6,045,575 A | | 4/2000 | Rosen et al. |
| 6,048,359 A | | 4/2000 | Biel |
| 6,063,108 A | | 5/2000 | Salansky et al. |
| 6,074,411 A | | 6/2000 | Lai et al. |
| 6,096,066 A | | 8/2000 | Chen et al. |
| 6,121,950 A | * | 9/2000 | Zavracky et al. ........... 345/101 |
| 6,238,425 B1 | | 5/2001 | Thiberg |
| 6,249,698 B1 | | 6/2001 | Parris |
| 6,273,883 B1 | | 8/2001 | Furumoto |
| 6,290,713 B1 | | 9/2001 | Russell |
| 6,302,900 B1 | | 10/2001 | Riggs |
| 6,370,019 B1 | * | 4/2002 | Matthies et al. ............ 361/681 |
| 6,436,127 B1 | | 8/2002 | Anderson et al. |
| 6,454,791 B1 | | 9/2002 | Prescott |
| 6,602,731 B2 | * | 8/2003 | Andriessen .................. 438/29 |

OTHER PUBLICATIONS

"Characterization of Epidermal Growth Factor Receptor and Action on Human Breast Cancer Cells in Culture" by Fitzpatrick, et al., Cancer Res. 44:3442–3447, Aug., 1984.

Lievens P., "The Influence of Laser Irradiation on the Motricity of Lymphatical System and on the Wound Healing Process", Intl. Congress on Laser in Med & Surgery, Bolgna Jun. 26–28, 1985.

Trelles M., Mayayo E., "Bone Fracture Consolidates Faster with Low Power Laser", Lasers in Surgery and Medicine, 7:36–45, 1987.

Karu, "Photobiological Fundamentals of Low–Power Laser Therapy", IEEE J. of Quantum Electronics, vol. QE23, No. 10, 1703–1717, Oct., 1987.

Karu, "Photobiology of Low–Power Laser Effects", Health Physics, 56:691–704, May 1989.

Airaksinen, O., et al. "Effects of He–Ne Laser Irradiation on the Trigger Points of Patients with Chronic Tension in the Neck", Scand J App Electronics, 4:63–65, 1989.

Zhao Y., et al., "He–ne Laser Irradiation Against Rat Adjuvant Arthritis", Jap J Assoc. Phys. Med. Balneol Climatol, 53#2:95–100, 1990.

Lombard A., et al., "Neurotransmitter Content and Enzyme Activity Variations in Rat Brain Following In–vivo He–ne Laser Irradiation", 1990 Proceedings, Round Table on Basic and Applied Research in Photobiology and Photomedicine, Bari Italy, Nov. 10–11th, 1990.

Smith K., "The Photobiological Effect of Low Level Laser Radiation Therapy", Laser Therapy, vol. 3, No. 1, 1991.

Baxter D., et al., "Low level laser therapy—Current clinical practice in Northern Ireland", Physiotherapy, 77:171–178, 1991.

Rossetti, et al., Neutransmitter aminoacid variations in rat brain after He–Ne laser irradiation, Laser & Technology, vol. 2, No. 2, 69–73, 1992.

Anders J., et al., "Low–power Laser Irradiation Alters the Rate of Regeneration of Rat Facial Nerve", Lasers in Surgery and Medicine, 13:72–82, 1993.

Telfer J., et al., "Leg Ulcers: Plastic Surgery Descent by Laser Therapy", Proc. of SPIE, 2086:258–261, 1993.

Laakso E., et al., "Plasma Acth and B–endorphin.Levels in Response to Low–level Laser Therapy (Lllt) for Mysfacial Trigger Points", Laser Therapy, 6:133–142, 1994.

Conlan, M.J., et al., "Biostimulation of Wound Healing by Low–energy Laser irradiation", J.Clin.Periodontol, 23:492–496, 1996.

Cowen, D., et al., "Low Energy Helium–neon Laser in the Prevention of Oral Mucositis in Patients Undergoing Bone Marrow Transplant: Results of a Double Blind Randomized Trial", Int.J. Radiat. Oncol. Biol.Phys., 38:697–703, 1997.

Yu, W., et al., "Effects of Photostimulation on Wound Healing in Diabetic Mice", Lasers in Surgery and Medicine, 20:56–63, 1997.

Gupta, A.K. et al., "The Use of Low Energy Photon Therapy (Lept) in Venous Leg Ulcers: a Double–blind, Placebo–controlled Study", Dermatol.Surg. 24:1383–1386, 1998.

Letter from Department of Health and Human Services to Randall Everett dated Sep. 22, 1998.

Berntsen, et al, "Stability of Polymer Light–emitting Diodes", Phillips J. Res. 51:511–525, 1998.

Chen, et al., "Molecular and Mechanistic Validation of Delayed Healing Rat Wounds as a Model for Human Chronic Wounds", Wound. Repair Regen. vol. 7, No. 6, 486–494, 1999.

Karu, T., "Primary and Secondary Mechanisms of Action of Visible to Near–ir Radiation on Cells", Journal of Photochemistry and Photobiology B: Biology, 49:1–17, 1999.

Whelan, et al., "Medical Applications of Space Light–Emitting Diode Technology—Space Station and Beyond", Space Technology and Applications International Forum, 1999.

Letter to the Editor in, Lasers in Surgery and Medicine 25:283, 1999 from Karu, T.

Reply to Letter to the Editor in, Lasers in Surgery and Medicine 25:284, 1999, from Lowe, et al.

Letter from Senator Arnold A. Mohl to Nadine Donahue of BioScan, Inc. dated Aug. 31, 1999.

Letter from Department of Health and Human Services to Butch Smith dated Jul. 18, 2000.

Fax Letter from Joseph E. Kutz, M.D. to Doctor Miller dated Jul. 27, 2000.

Press Release "NASA Space Technology Shines Light on Healing" Release: 00–336 Marked: "For Release Dec. 18, 2000".

Whelan, H.T. et al., "Effect of Nasa Light–emitting Diode Irradiation on Wound Healing", J.Clin.Laser Med. Surg., vol. 19, No. 6, 305–314, 2001.

Mikhael, et al., "Large–area Flexible Light Sources, Extended Abstracts"—Title later changed to "Self–Healing Flexible Photonic Composites for Light Sources", $1^{st}$ Intl. Conf. Sci, & Technol. Emissive Displays Lighting, SID, San Diego, CA, Nov. 12–14, 2001.

Whelan, et al., "NASA Light Emitting Diode Medical Applications From Deep Space to Deep Sea", Space Technology and Applications International Forum, 2001.

Karu, et al., "Cell Attachment to Extracellular Matrices is Modulated by Pulsed Radiation at 820 nm and Chemicals that Modify the Activity of Enzymes in the Plasma Membrane" Lasers in Surgery and Medicine 29:274–281, 2001.

Torricelli, et al., "In Vivo Optical Characterization of Human Tissues from 610 to 1010 Nm by Time–resolved Reflectance Spectroscopy", Physics in Medicine and Biology 46:2227–2237, 2001.

Chwang, et al., "Efficient and Stable Graded Mixed Layer Organic Light Emitting Devices, Extended Abstracts", presented at the 1st Intl. Conf. Sci, & Technol. Emissive Displays Lighting, SID, San Diego, CA, Nov. 12–14, 2001, (Copy of conference proceedings unavailable, but the substance of the presentation is believed to have been published later as "Graded Mixed–Layer Organic Light–emitting Devices" in Applied Physics Letters—see reference below).

Shim, et al., "Degradation of Organic Light–emitting Devices Due to Formation and Growth of Dark Spots", Matl. Sci. Eng. B85: 154–159, 2001.

Bhatti M., et al., "Identification of Photolabile Outer Membrane Proteins of Porphyromonas Gingivalis", Cur. Microbiol. 43:96–99, 2001.

Chwang, et al., "Graded Mixed–layer Organic Light–emitting Devices", Applied Physics Letters, vol. 80, No. 5, Feb. 4, 2002.

Call for Collaboration by International Medical Instruments Inc., 2002.

Flyer Advertisement "Bioscan" by: BioScan, Inc., undated.

"Laser Therapy Introduction", Company Website Address: http://www.laser.uk.com/intro/index.html, undated.

"Cos–Medic Photon Facial Controls and Specifications", Company Website Address: http://www.diomedics.com/cosspecs.htm, undated (printed in 2001).

BioScan, Inc. Products, Company Website Address: http://www.bioscanlight.com/new_pages/humanlight.htm, undated (printed in 2001).

BioScan, Inc. Company Website Address: http://www.bioscanlight.com/unt_flash.htm, undated.

"Performance Horse Therapy –Making Horse Calls", Company Website Address: http://www.painx2000equinetherapy.com/product.html, undated (printed in 2001).

"InfraRed Muscle & Tendon Relaxer", Company Website Address: http://www.ioa.com/~dragonfly/relaxerinfo.html, undated (printed in 2001).

"Your Winning Advantage Speeds Recovery", Company Website Address: http://www.theralaser.cyberproduct.com/default.htm, undated (printed in 2001).

"Head Light", Company Website Address: http://www.beyond2000.com/news/Dec 00/story 932.html, Apr. 4, 2001.

* cited by examiner

PHOTOTHERAPEUTIC TREATMENT METHODS AND APPARATUS

FIELD OF THE INVENTION

This invention relates generally to the field of phototherapy. More particularly, this invention in certain embodiments relates to methods and apparatus for phototherapy using a thin film electroluminescent (TFEL) light source.

TABLE OF AUTHORITIES

The following authorities are cited by number in the text follow:
1. Whelan, H. T. et al., Effect of NASA light-emitting diode irradiation on wound healing, J.Clin.Laser Med.Surg. 19:305–314, 2001
2. Karu, T., Primary and secondary mechanisms of action of visible to near-IR radiation on cells, 49:1–17, 1999
3. Karu, T., The Science of Low-Power Laser Therapy, Gordon and Breach Sci. Publ., 1998
4. Gupta, A. K. et al., The use of low energy photon therapy (LEPT) in venous leg ulcers: a double-blind, placebo-controlled study, Dermatol.Surg. 24:1383–1386, 1998;
5. Cowen, D., et al., Low energy Helium-Neon laser in the prevention of oral mucositis in patients undergoing bone marrow transplant: results of a double blind randomized trial, Int.J. Radiat.Oncol. Biol.Phys., 38:697–703, 1997.
6. Yu, W., et al., Effects of photostimulation on wound healing in diabetic mice, Lasers Surg.Med. 20:56–63, 1997.
7. Norman Salansky and Natalia Filonenko, U.S. Pat. No. 6,063,108, Method and Apparatus for Localized Low Energy Photon Therapy.
8. Conlan, M. J., et al., Biostimulation of wound healing by low-energy laser irradiation. A review, J.Clin.Periodontol., 23:492–496, 1996
9. Trelles M., Mayayo E. Bone fracture consolidates faster with low power laser. Lasers Surg Med, 1987;7:36–45.
10. Lievens P., The influence of laser irradiation on the motricity of lymphatical system and on the wound healing process. Intl. Congress on Laser in Med & Surgery, Bolgna Jun. 26–28, 1985.
11. Telfer J., et al., Leg ulcers: Plastic surgery descent by laser therapy. Proc. of SPIE, 1993;2086:258–261.
12. Companies Internet Web sites: http://www.bioscanlight.com/unt_flash.htm; http://www.painx2000equinetherapy.com
13. Smith K., The Photobiological Effect of Low Level Laser Radiation Therapy, Laser Therapy, Vol. 3, No. 1, 1991
14. Torricelli, A., et al., In vivo optical characterization of human tissues from 610 to 1010 nm by time-resolved reflectance spectroscopy, Phys.Med.Biol. 46(2001) 2227–2237
15. Karu, Health Physics, 56:691–704, 1989; Karu, IEEE J. of Quantum Electronics, QE23:1703–1717, 1987.
16. Dew, D., U.S. Pat. No. 4,672,969, Laser healing method
17. Airaksinen, O., et al. Effects of He—Ne laser irradiation on the trigger points of patients with chronic tension in the neck. Scand J App Electrother, 1989;4:63–65.
18. Trelles, M., et al., Bone fracture consolidates faster with low power laser. Lasers Surg Med, 1987;7:36–45.
19. Anders J., et al., Low-power laser irradiation alters the rate of regeneration of rat facial nerve. Lasers Surg Med, 1993;13:72–82.
20. Lievens P., The influence of laser irradiation on the motricity of lymphatical system and on the wound healing process. Intl. Congress on Laser in Med & Surgery, Bolgna Jun. 26–28, 1985.
21. Zhao Y., et al., He—Ne laser irradiation against rat adjuvant arthritis. Jap J Assoc. Phys. Med. Balneol Climatol, 1990;53#2:95–100.
22. Baxter D., et al., Low level laser therapy. Current clinical practice in Northern Ireland. Physiotherapy, 1991;77:171–178.
23. Lombard A., et al., neurotransmifter content and enzyme activity variations in rat brain following in-vivo He—Ne laser irradiation. 1990 Proceedings, Round Table on Basic and Applied Research in Photobiology and Photomedicine, Bari Italy, November 10–11th.
24. Laakso E., et al., Plasma ACTH and B-endorphin levels in response to low-level laser therapy (LLLT) for mysfacial trigger points. Laser Ther, 1994;6#3:133–142.
25. Prescott, M. A., U.S. Pat. No. 5,989,245, Method and apparatus for theraupeutic laser treatment.
26. Bhafti M, Nair S P, Macrobert A J, Henderson B, Shepherd P, Cridland J, Wilson M., Identification of photolabile outer membrane proteins of Porphyromonas gingivalis, Curr. Microbiol. 43: 96–99, 2001.
27. Prescott M., Laser therapy for foot conditions, U.S. Pat. No. 6,454,791.

BACKGROUND OF THE INVENTION

Phototherapy (PT) relates to the use of electromagnetic radiation to stimulate biological phenomena that promotes healing or aesthetic changes in tissue. In the early 1960s, European scientists began studies on the use of low energy light beams of specific wavelengths and frequencies to treat damaged cell tissue by altering cellular functions and enhancing healing non-destructively. Low level laser therapy (LLLT) followed by light emitting diode (LED) therapy were developed and applied to the treatment of dermatological, musculoskeletal, soft tissue and neurological conditions. It is well documented now that a wide range of disorders of biological tissue or their symptoms have been treated by PT [1–26], including but not limited to acute and chronic musculoskeletal conditions such as arthritis, degenerative disc and joint diseases, bone spurs, back and joint pain, tendonitis, muscle pain and stiffness and myofascial pain. PT has also been used to treat such conditions as post surgical complications such as swelling, inflammation, scarring and stiffness; acute trauma and chronic post-traumatic conditions in the soft tissues and bones including sprains, strains, wounds, whiplash; repetitive strain injuries such as carpal tunnel syndrome, tennis and golfer's elbow; neurological and neuromuscular conditions, dermatological conditions such as burns, acne, herpes simplex, psoriasis, skin cancer and ulcers including infected or non-infected chronic ulcers of different etiology such as venous ulcers, diabetic ulcers, decubitus ulcers, pressure sores, burns and post-traumatic ulcers, as well as seasonal depression. PT has also been reported to reduce wrinkles, and induce relaxation.

In a study funded by a NASA Small Business Innovation Research contract, Whelan and his team [1] studied the influence of PT treatment using LEDs on cells grown in culture, on ischemic and diabetic wounds in rat models, and on acute and chronic wounds in humans. Their studies utilized a variety of LED wavelengths, power, and energy density to identify conditions for biostimulation of different tissues. They found that PT using LEDs produced in vitro increases of cell growth of 140–200% in mouse-derived fibroblasts, rat-derived osteoblasts, and rat-derived skeletal muscle cells, and increases in growth of 155–171% of normal human epithelial cells. PT using LEDs produced improvement of greater than 40% in musculoskeletal training injuries in Navy SEAL team members, and decreased wound healing time in crew members aboard a U.S. Naval submarine. Lacerations doubled their healing rate when exposed to the LED light. Some injuries treated with the LEDs healed in just seven days, compared to unexposed injuries that took two weeks. Whelan and colleagues also found that lights help wounds that are normally very difficult to heal such as diabetic skin ulcers, serious burns and the severe oral sores caused by chemotherapy and radiation [1]. Their investigations take place in laboratory and human trials, approved by the U.S. Food and Drug Administration.

Recent in vivo and clinical studies suggest that lasers can induce phenomena in injured tissues which promote acceleration of recovery after acute trauma [19–21]. Faster edema reduction and lymph flow enhancement were observed in laser-treated animals after surgery in mice [20] and rat arthritis [21]. Faster edema resolution and regeneration at cut blood and lymph vessels were observed in the laser treated group in the study performed on 600 mice [20]. It was also found that laser light induced local microcirculation improvement resulting in relief of local spasm of arteriolar and venular vessels, intensification of blood flow in nutritional capillaries, anastomosis opening and activation of neoangiogenesis [17].

One of the best documented PT treatments that has been in routine use in hospitals for many years, is the treatment of hyperbilirubinemia, a condition where there is an elevated level of bilirubin in an infant's blood. Normally bilirubin is conjugated within the liver and excreted. However, during the initial neonatal period the infant's liver may be too immature to conjugate bilirubin. Phototherapy is the treatment of choice for neonatal hyperbilirubinemia and has been used for many years with no known negative side effects. Bilirubin has absorption bands in the visible wavelengths region of the spectrum between 400 and 500 nm with a maximum absorption approximately in the 450–460 nm region. There is a clear dose-response relationship as demonstrated by a decrease in the bilirubin level proportional to the level of exposure to light.

Ultraviolet (UV) radiation has been used to treat dermatological diseases such as psoriasis since the early 20$^{th}$ century. However, UV radiation produces ionization and therefore has the potential to damage biomolecules. As a result, the dosage or exposure must be controlled carefully to avoid damage to biological tissue.

There are also reports on successful treatment of aesthetic problems, using PT. Particularly, decreasing of cellulites and wrinkles when treated with radiation of selected wavelength in the visible and NIR part of the spectrum has been reported.

Quite recently, the combined approach of using light as a very specific mechanism to trigger the effects of specialized pharmaceuticals has been developed. This approach, called photodynamic therapy (PDT) uses certain drugs, which for example are preferably adsorbed at tumors which, when irradiated with visible light, initiate cytotoxic photochemical reactions that produce local tumor necrosis. Another recent application of PDT is the use of photosensitizer drugs that exert an anti-microbial effect only when irradiated with light of a certain wavelength. Activated with light, the drug produces potent anti-microbial molecules that kill neighboring micro-organisms, mainly by physically damaging their cytoplasmic membranes [26]. Most photosensitive substances used in photodynamic therapy are activated at wavelengths between 300 nm and 800 nm. Light emitting diodes are typically used to treat surface conditions while a laser coupled to a fiber optic catheter is often used to treat sub-surface regions. Subcutaneous tissue may also be treated using an external light source that emits light at a wavelength that penetrates the cutaneous layer overlying the tissue to be treated.

Currently, therapeutic benefits have been reported for wavelengths ranging from UV radiation to the near-infrared (N-IR) region of the spectrum [1–26]. Current research suggests that when phototherapy is used within this wide range of wavelengths for treatment of a particular medical condition, light may interact with tissue at the molecular, cellular, and organism levels. At a molecular level, light therapy methods are based on photochemical conversion of non-specialized photoacceptor molecules (i.e. molecules that can adsorb light at certain wavelengths but are not incorporated into the light reception organs). These non-specialized photoacceptors can be cell native components or can be introduced artificially, as in a case of photodynamic therapy. In the case of adsorption of light of a specific wavelength by a native photoacceptor with corresponding excitation of their electronic states, the cellular metabolism can be altered [2,3]. More specifically, Karu [2,3, 15] suggested that irradiation of isolated mitochondria induces changes in cellular homeostasis, which entail a cascade of reactions, and proposed a number of the components of the respiratory chain that can trigger the reactions. Currently it is speculated, that the biological effects of low level visible light is through photochemistry (probably electronic excitations of enzymes [2,3,15]), and the biological effect of infrared radiation is due to photophysical effects on the cell membrane level, mainly through molecular rotation and vibrations modifying the ion channels in membranes [13] that influence the total cascade of molecular events and leads to biostimulation.

In order to identify a photoacceptor molecule, experiments on cell cultures were performed to obtained action spectra, which is a plot of the relative efficiencies of different wavelengths of light in causing a biological response (such as proliferation, migration, collagen synthesis, autocrine production of growth factors etc.) [1,2,3]. It is known [2] that within certain limits an action spectrum follows the absorption spectrum of the photoacceptor molecule. By comparison the obtained absorption spectrum of cells with spectral data for particular metal-ligand complexes corresponding to different candidate photoacceptors, the enzymes, participating in the biological response, can be identified. As no action spectra for clinical effects have yet been produced, action spectra for cellular effects are currently used to recommend optimal light wavelengths for clinical applications. Experiments on different cell cultures (microbe and mammalian) have revealed the ranges of wavelengths (360–440 nm, 630–680 nm, 740–760 nm, 810–840 nm) where known photoinduced phenomena are observed [2,3].

Ideally, in clinical applications photons of a particular wavelength excite photoacceptor molecules providing the desired biological response. The light should generally be capable of reaching not only superficial tissue but also deeper layers. In order to arrive at a particular treatment protocol, in addition to the action spectra of various photobiological effects and absorption spectra of photoacceptor molecules responsible for these photobiological effects, the following data can also be taken into account: (1) absorption spectra of the surrounding tissue light adsorbing molecules, and (2) wavelength penetration depth data.

The light absorbed by biological tissue depends on the wavelength of the light and the properties of the irradiated tissue. Factors such as reflectivity, absorption coefficient, and scattering coefficient determine the dose versus depth distribution of the incident light. In biological tissue, hemoglobin is a strong absorber of light in the visible region of the spectrum while water has several strong absorption bands in the IR region. Thus the absorption bands of these two molecules should be considered in selecting a wavelength that will pass substantially unattenuated through tissue to deliver the desired radiation to the area to be treated. The dose will also vary as a function of depth due to absorption.

In general, each condition being treated by phototherapy may utilize unique settings of treatment parameters such as wavelength, monochromaticity, bandwidth, pulse frequency, pulse duration, power intensity, dose, and three-dimensional light distribution in the tissue. An extensive summary of suggested protocols developed for treatment of a wide range of disorders is provided in the patent of Salansky and Filonenko [7].

For different applications, different wavelengths might be optimal. Regarding the DNA and RNA synthesis in cell-level experiments, Tiina Karu [2,3] suggested that laser emission at 820–830 nm, 760 nm and 680 nm would be sufficient for low power light therapy. According to the patent by Salansky and Filonenko [7] clinical studies reveal that wavelengths in the range from 400 to 10,000 nm may be used for PT, preferably from 500 to 2,000 nm. There appears to be some optimal wavelength range to induce a particular photoeffect for certain healing phenomenon. For example, according to [7], light having a wavelength from 600 to 700 nm, preferably from 630–680 nm, may be used for wound and ulcer healing. For chronic soft tissue pathology, monochromatic light in the near infrared wavelength range (800–1,100) is more suitable [7]. In general, different researchers in the area of phototherapy have used light at the following wavelengths (nm) for phototherapy: 470, 565, 585, 595, 620, 635, 645, 655, 660, 700, 830, 840, 880, 910, 920, 940.

A phototherapeutic dose is determined by a light intensity (power density) and an exposure time. For stimulating healing of chronic ulcers or wounds, a power density has been reported in the range from 0.2 to 10 mW/cm$^2$. For ulcers or wounds in the acute inflammatory stage the range was from 10 to 30 mW/cm$^2$ and for infected wounds the range was from 50 to 80 mW/cm$^2$ [7]. Reported doses for photobiomodulation are in the range of from 0.1 to 20 J/cm$^2$ [7]. For stimulating healing of chronic ulcers or wounds doses may preferably be in the range of from 0.05 to 0.2 J/cm$^2$, for ulcers or wounds in the acute inflammatory stage a preferred range is from 2 to 5 J/cm$^2$ and for infected wounds a preferred range is from 3.0 to 7.0 J/cm$^2$.

It has been also reported that the interaction between living cells and pulsed electromagnetic waves depends on the wavelength as well as pulse frequency and duration. Pulse repetition rates within the range 1,000–10,000 Hz with different pulse durations (milliseconds to microseconds) can be used to change average power [7]. Low range frequencies of 0 to 200 Hz may stimulate the release of key neurotransmitters and/or neurohormones [7]. It has been theorized that these frequencies may correspond to some basic electromagnetic oscillation frequencies in the peripheral and central nervous system. Once released these neurotransmitters and/or neurohormones can modulate inflammation, pain or other body responses.

Optical protocols have been developed based on the parameters described above. Protocols for a wide variety of disorders have been developed for laser diodes, superluminescent diodes, and LED single probes or clusters, for example by Salansky [7]. They have been used in the 'Pain & Injury Rehabilitation Centers', Toronto, Canada. For example, the specificity of protocols for musculoskeletal conditions depends on (i) the stage of inflammatory process (acute, subacute inflammation, chronic inflammation with or without flare-up of preexisting pathological condition); (ii) localization of soft tissue affected areas, muscle spasm, tender and trigger points. For skin conditions, choice of a protocol can depend on the stage of inflammation (acute or chronic inflammation, presence or absence of bacteria contamination). Protocols developed by Salansky for laser diodes usually take about two to six minutes; it rarely exceeds ten minutes. Whelan [1] used LED therapy at 680, 730, and 880 nm wavelengths simultaneously for about 30 minutes per treatment in human trials. In general, the duration of treatment depends on the power of a light source, with longer times being used with sources of lower power density.

The areas of phototherapy and photodynamic therapy are undergoing rapid development. Yet, a detailed understanding of the mechanism that produces the beneficial effect has not been achieved in many treatments.

There are several sources of radiation currently used for phototherapy and aesthetic applications. The He—Ne laser ($\lambda$=632.8 nm) was the first laser to be used in clinical and research applications from the sixties to mid-eighties, when semiconductor lasers and light emitting diodes became available [3]. "Cold" lasers produce a lower average power of 100 milliwatts or less. Lasers are widely used in phototherapy because they produce narrow-band monochromatic, coherent, polarized light with a wide range of powers and intensities. High-power is used in surgery and mid-power is used in dermatology to treat, for example, telangiectasia, port-wine stains. Lasers must be used cautiously to avoid or achieve limited heating of tissues except when higher powers are desired for use in surgery, dermatology, etc. Coherence and polarization are the two main features that distinguish light from lasers from other sources of monochromatic light. But, laser beams quickly lose coherence and polarization due to scattering upon entering tissue. So, many of the reputed advantages due to these properties of laser beams may be lost. A common laser beam source in current PT applications is the semiconductor laser diodes (LD), where light emission arises from recombination of electron and holes injected into a lasing cavity. Recently, vertical cavity surface emitting lasers had been also suggested for use in PT devices [27]. Although phototherapy began with the use of low level lasers, several other light sources have been used since that time, that are briefly outlined below.

Light emitting diodes are semiconductor devices in which a point source of light is produced when current carriers combine at a pn junction. The emission is spontaneous and the output power is typically lower than that from diode lasers, reflecting the use of lower operating currents. Generally LEDs are less expensive than diode lasers and can operate at shorter wavelength without the rapid degradation that occurs with visible-wavelength laser diodes. Light from an LED is an incoherent (spontaneous) emission, as distinct from the coherent (stimulated) emission produced by lasers. LEDs have undergone a major growth spurt in recent years. The first LED units available for purchase for use in PT in the equine industry [3] used 8mW peak power per diode. At this writing, devices are commercially available which use a cluster of LEDs with 150 mW peak power per diode. Another PT light source, superluminous diodes are a compromise between a laser and a LED, which is operated at high drive currents characteristic of diode lasers, but lack the cavity feedback mechanisms that produce stimulated emission. It is used when high-power output is desired, but coherent emission is not needed. Both LEDs and LDs are three-dimensional semiconductor structures that produce point sources of light.

The conventional light sources used in photobiological studies as well as in phototherapy are incandescent lamps, fluorescent lamps, and electric arcs. It is generally necessary to monochromatize their continuous spectrum. This is accomplished with either a monochromator (with bandwidth 5–10 nm) or filters. Conventional light sources are usually used in laboratory work for recording of action and absorption spectra or obtaining a wavelength which is not emitted by available lasers or LEDs [3].

Conventional PT devices (based on LD and LEDs) are generally configured into a hand-held probe with a single or a few point sources of light or a large stationary probe having an array of lasers for clinical use. Since LDs and LED sources of radiation are small three-dimensional semiconductor devices that act as point sources of light, they cannot provide uniform doses of radiation over the treated surface of the body. To solve this problem, light diffusers are used. When several specific wavelengths are required, several types of laser diodes or LEDs with different emission wavelengths are used within an array, making it yet more difficult to achieve uniform irradiation of a particular wave length. LD or LEDs array mounted on a substrate possess its own circuitry with wiring required to each individual LED or LD. LED arrays also generally require a cooling mechanism.

BRIEF DESCRIPTION OF THE DRAWINGS

The features of the invention believed to be novel are set forth with particularity in the appended claims. The invention itself however, both as to organization and method of operation, together with objects and advantages thereof, may be best understood by reference to the following detailed description of the invention, which describes certain exemplary embodiments of the invention, taken in conjunction with the accompanying drawings in which:

DETAILED DESCRIPTION OF THE INVENTION

Figure 1:
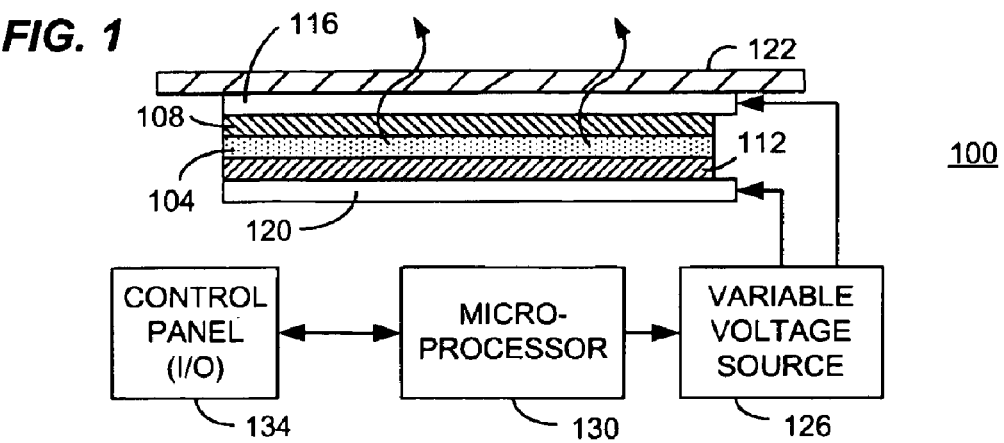
FIG. 1 is a cross-sectional view of a thin film electroluminescent light source and associated circuitry consistent with certain embodiments of the present invention.

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open ended language). The term "coupled", as used herein, is defined as connected, although not necessarily directly, and not necessarily mechanically. The term "program", as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system.

The term "phototherapy", as used herein is intended to embrace both phototherapy and photodynamic therapy. The term "infrared" as used herein is intended to encompass the range of light spectrum above approximately 650 nm and includes regions often termed "near-infrared". "Transparency" as used herein is defined as passing a substantial portion of light at a wavelength of interest, while "reflectivity" is similarly defined as reflective of a substantial portion of light at a wavelength of interest. The term Thin Film Electroluminescence (TFEL) as used herein should be interpreted to mean electroluminescent (EL) devices that are made of stacked layers that are substantially planar in that the thickness of their essential light creation components is much smaller than their other dimensions. This term is intended to embrace inorganic high field EL devices as well as organic light emitting devices (OLEDs) (whether a dopant is used in the active layer or not), which can be made with major dimensions ranging from millimeters to several inches and beyond. The term TFEL specifically excludes conventional inorganic semiconductor laser and conventional inorganic semiconductor diode devices such as LEDs and LDs (which may broadly fall within certain definitions of EL sources). The term TFEL also clearly specifically excludes incandescent lamps, fluorescent lamps and electric arcs. The term EL as used herein, is generally intended to mean TFEL. The term "dopant" as used herein can mean a dopant atom (generally a metal) as well as metal complexes and metal-organic compounds used as an impurity within the active layer of a TFEL device. Some of the organic-based TFEL active layers may not contain dopants. The term LED as used herein is intended to mean conventional inorganic (e.g., doped silicon based) semiconductor light emitting diodes. The term "OLED" is intended to exclude such conventional inorganic semiconductor LEDs, even though an OLED is often referred to as a type of organic based light emitting diode.

As described above, phototherapy has been used to treat various medical and aesthetic conditions for some time. The field of phototherapy is in a state of rapid experimentation and development at the present time. The light sources used for phototherapy, as it has been outlined above, are often based upon light emitting diode technology which is one of two classes of EL devices in which the production of light is based upon the non-thermal conversion of electrical energy into luminous energy. In LED devices, light is generated by electron-hole pair recombination near a p-n junction. LEDs are typically point sources with a typical size of LED chip die ~0.4 mm (0.016") in all three directions (i.e., the devices are not considered planar). The anode and cathode contacts usually are opposite each other on the top and bottom of the die. The bottom of the dye with a bottom electrode is usually attached to a conductive substrate using conductive adhesive. Light sources for phototherapy based upon LEDs are generally fabricated in an array in order to produce adequate light to illuminate a significant region of tissue. The typical distance between LED light sources in 2-dimensional arrays is about 1 cm×1 cm. The LED's are selected according to their wavelength of light generation and range from various colors in the visible spectrum to near infrared and infrared.

Such LED arrays suffer from several drawbacks. They generally require a diffusing element to produce uniform emission since a LED illuminator panel is composed of individual LEDs which produce points of light that are fabricated into an array. Also, the LED panel requires electrical wiring to each individual element making the illuminator somewhat complex and expensive to manufacture. LED arrays also commonly generate enough heat to require a cooling mechanism.

The present invention provides an illuminator for phototherapy or photodynamic therapy that can be positioned in close proximity to or in direct contact with the tissue or skin of the patient or the light output coupled to a fiber optic catheter for in-vivo treatment. In certain embodiments consistent with the present invention, the illuminator has a thin, lightweight TFEL panel designed to provide uniform illumination over the area to be treated without the use of diffusers that would attenuate a portion of the light output. A single illuminating unit can be used as a TFEL panel requiring only two electrodes with two electrical connections, and can be made as large as several inches by several inches or even several feet by several feet. This is a dramatic difference from pointed single illuminating arrays used in previous PT devices. The illuminator may be operated in a range of power and frequency that does not generate excessive heat so that the illuminator surface may be used in contact with the patient's skin without discomfort and without need for the use of a cooling mechanism. The illuminator can be designed to emit light with wavelengths ranging from the visible to the infrared range. Selection of the appropriate wavelength allows the optimization of the illuminator for specific treatments.

Turning now to FIG. 1, an exemplary TFEL panel and associated circuitry consistent with certain embodiments of the present invention is illustrated as 100. For purposes of the current discussion, start by assuming that this is an inorganic high field EL device. In this simple embodiment, a thin film electroluminescent panel is fabricated by sandwiching an inorganic electroluminescent layer 104 between two transparent insulators 108 and 112, which are further sandwiched between a pair of electrodes 116 and 120. The seal material (glass or polymer) 122 covers the light emitting portion of the device and protects the user from the high voltage used to spawn the generation of light. In one embodiment, the layer 122 also serves as a substrate for the growth of thin films of the materials composing the TFEL panel. When layer 122 serves only as a seal material, the substrate supporting the thin films can be placed beneath the bottom electrode 120. This produces a single illuminating unit requiring only two electrodes that can be as large as several inches by several inches and even several feet by several feet.

In this exemplary embodiment, an active inorganic electroluminescent layer 104 generates light by impact excitation of a light-emitting center (called the activator or dopant), embedded in a host material, by high-energy electrons. Since the electrons gain their energy from an electric field (1–2 MV/cm), this type of EL is often called high field electroluminescence (HFEL). A host matrix with an activator in this embodiment can be in the form of inorganic thin film or powder doped with a metal ion (ions) or metal complex (complexes). In general, the host material has a band gap large enough to emit light without absorption as well as to provide a medium for the efficient transport of high energy electrons. Examples of the inorganic host matrix include, but are not limited to, ZnS and SrS (currently most popular), ZnGa2O4, ZnSiO4, CaSSe, CaS and others. Example of active centers incorporated in the EL phosphor material include, but are not limited to: Mn, Cu as well as rear earth elements (such as Ce, Nd, Sm, Eu, Tb, Tm, Er, Nd and others) and their complexes (TbOF and others).

To enhance the efficiency and shift the peak emission wavelength, co-doping can be also used (for example, Ag in SrS:Ce,Ag blue EL phosphor). The insulators 108 (for example, ATO—a mixture of $TiO_2$ and $Al_2O_3$) and 112 (for example, the Barium Tantalate, $BaTa_2O_4$) on either side of the active layer limit the maximum current to the capacitive charging and discharging displacement current level. Electrodes sandwiching the insulator and EL layers form a basic capacitive structure. Electrode 116 is a transparent conductive electrode such as, for example, an Indium Tin Oxide (ITO) electrode, that permits light of a certain wavelength range to pass. Alternate electrode materials, such as nickel-cobalt spinel oxide, may be used to extend the range of transparency further into the IR range.

Electrode 120 is preferably somewhat reflective (for example, Al) so that light that is incident on electrode 120 will reflect back through electrode 116. In certain embodiments consistent with the present invention, the electrode closer to the area to be treated in the TFEL illuminator is transparent while the second electrode serves as a reflector. Light emitted in the phosphor layer is uniform in all directions. The reflecting electrode serves to reflect light generated in the phosphor layer emitted in that direction as well as any light reflected from the patient's skin not absorbed by the other layers in the TFEL structure. Due to the reflective properties of the electrode, the overall illuminator efficiency is improved. The highest luminance reported in flat panel display industry for TFEL panel (pixeled) with inorganic emission layer in the visible region of light spectrum currently is >1000 $cd/m^2$ (>1 $mW/cm^2$).

A typical thickness of the TFEL panel not counting a substrate is ~1.5 $\mu$m. A typical thickness of a glass substrate in an EL device is ~1 mm. Thus the illuminating panel can be made to be very light and compact. This structure can be extended in width to produce a TFEL panel that is large in area and somewhat planar with a very thin cross section. Yet wiring to such a device may remain as simple as a two-wire connection.

In another embodiment consistent with the invention, the active layer of the TFEL is an organic-based material. Organic-based electroluminescent light (OEL) sources have been under development for several years and may be particularly attractive for PT applications because of their very simple fabrication techniques (for example, spin on coating of organic material), high brightness emission in the visible and IR part of the spectrum and low operational voltage. The high brightness makes OEL displays attractive as a source of radiation and the low voltage operation allows the OEL sources to be battery powered, which enhances their portability and ease of use in the field.

FIG. 1 can also represent the structure of an OEL. In this case, the active layer 104 is an organic material as will be described later. The electrodes 116 and 120 are similar or identical in structure to that of the inorganic HFEL source previously described. Instead of insulating layers 108 and 112, the OEL often uses an electron/(or hole) injection/(or blocking) layer that are similarly located. Additionally, the organic material forming the active layer may be made up of multiple layers and may or may not have a dopant.

Currently, the typical luminance of OEL sources ranges from several hundreds to several thousands $cd/m^2$ with the highest luminance currently reported >40000 $cd/m^2$ (corresponding to ~40 $mW/cm^2$) in the region of visible light have been demonstrated from such displays. A large variety of polymers, copolymers and their derivatives has been demonstrated within last the decade to posses EL properties. The configuration of such polymer-based devices may have a simple single layer, bilayers, or blends of polymers used to enhance efficiency, tune the emission wavelength or even provide devices that emit light of different colors simply by changing the driving voltage. In the last case, as an example, a blend of two polythiophene-based polymers can be cited, which posses two different bandgaps and thus different emission colors and different turn-on voltages. As described above, a typical single layer polymer organic TFEL is constructed by sandwiching a thin layer of luminescent conjugated polymer between an anode and cathode, where one electrode is transparent. Organic materials can be also be made up of emitting metal containing organic compounds (for example, aluminum tris(8-hydroxyquinoline) incorporated to the polymer host matrix also have been employed as OEL materials for generating visible light. When containing rare earth ions, emission from metal containing organic compounds often exhibit sharp peaks in both visible and NIR spectral regions. Relatively recently, organolanthanide phosphors have been demonstrated to give high enough brightness and efficiency to underline their potential for use in OEL devices. Organic TFEL devices are sometimes referred to as an OLED (Organic Light Emitting Device or Organic Light Emitting Diode), In one embodiment consistent with the present invention, organic-based TFEL panel 100 has a layer 122 that forms a supporting substrate (glass or polymer) and that also serves as a sealing material protecting the organic material from degradation, a transparent conducting electrode 116 (such as, for example, ITO), a hole transport conducting polymer layer 108 (such as, for example PEDOT-PSS), the active light emitting layer 104, and the top electrode structure in the form of a calcium layer 112 and aluminum layer 120, where Ca and Al can be substituted by other conductive materials with relatively low work function. The emitting layer can be, for example, made of blends of MEH-PPV or PPP-OR11 with lanthanide-TPP complexes, where lanthanide can be Yb (peak emission at 977 nm), Er (1560 nm) and others.

Another embodiment consistent with the invention of the OEL device emitting red light (612 nm peak) can have the following layers: glass (polymer) substrate/ITO/Eu(TTFA) 3(phen):PBD:PVK/BCP/Ca/Al. In this embodiment, a new functional layer—BCP, is incorporated as a hole-blocking layer substantially improving brightness and efficiency. In general, in addition to the layers of materials described above, additional layers for OEL device can be incorporated, such as electron or hole injection or blocking layers. Other configurations are also possible without departing from the present invention.

In both inorganic and organic-based TFEL devices, a single emitting unit driven by two electrodes can be substantially large due to much lower current generated in these structures as compared to semiconductor LEDs. A single illuminating unit requires only two electrodes but can be as large as several inches by several inches and even several feet by several feet. The current within high field inorganic EL and OELs range from several $mA/cm^2$ to ~100 $mA/cm^2$, while for semiconductor LEDs it is ~100 $A/cm^2$.

Light is generated in inorganic TFEL device 100 by application of an AC voltage across electrodes 116 and 120 of sufficient magnitude to cause emission of light by the active layer 104. (DC could be used but at the expense of higher current drain.) Electrical charge is injected into the active layer, by application of voltage across the electrodes, exciting the dopant atoms. Relaxation of the dopant atoms back to the ground state results in the emission of photons characteristic of the dopant atom and the phosphor host. The wavelength of the light emitted is determined by the dopant or dopants in the active layer. Each dopant used in the TFEL panel will exhibit a unique spectral output characteristic of that dopant. Often, if a single dopant is used, light will be emitted predominantly at a single wavelength, but often a single dopant will also result in multiple dominant lines in the output frequency spectrum. Multiple dopants, perhaps currently as many as about three, but this should not be considered limiting, can be effectively used to generate light at multiple wavelengths or spectra.

Historically inorganic TFEL devices have been optimized for emission in the visible wavelength range specifically for display applications using, for example dopants such as copper to produce blue emission and manganese to produce amber emission. However, it has been recently discovered that by doping the phosphor layer with a rare-earth element a strong EL emission band is often produced in the infra-red range accompanied in many cases by some level of emission in the visible range. The selection of the appropriate dopant allows the characteristic EL emission to be changed to wavelengths ranging from the visible to the infrared. The spectrum can also be modified somewhat by annealing. The emission is characteristic of the specific dopant used. The use of two or possibly three or more dopants can be utilized to produce multiple characteristic emission lines. The wavelengths may be chosen to match the portions of the electromagnetic spectrum known to have therapeutic benefit in phototherapy or to activate the photoreactive agent in photodynamic therapy. Some illustrative dominant wavelengths associated with several dopants are given by TABLE 1 below (but this listing should not be considered exhaustive or limiting in any sense, but merely illustrative of the ability to produce EL emissions in the range of wavelengths considered useful for known phototherapy applications. Other dopants are continuously being tested to find new light characteristics.):

TABLE 1

| INORGANIC AND ORGANIC EL MATERIAL (MATRIX:DOPANT) | DOMINANT LIGHT WAVELENGTHS EMITTED FROM EL SOURCE |
| --- | --- |
| ZnS:Tm (Thulium) | 480 nm and 800 nm |
| ZnS:Nd (Neodymium) | 890 nm |
| ZnS:Er (Erbium) | 550, 660 and 980 nm |
| ZnS:Mn | 580 nm (yellow) |

TABLE 1-continued

| INORGANIC AND ORGANIC EL MATERIAL (MATRIX:DOPANT) | DOMINANT LIGHT WAVELENGTHS EMITTED FROM EL SOURCE |
| --- | --- |
| SrS:Cu | 475 nm (green/blue) |
| (SrS:Cu, Ag) | (430 nm) (blue) |
| SrS:Ce | 510–550 nm double peaked |
| Eu(TTFA)$_3$(phen):PBD:PVK | 612 nm (red) |
| Yb(TPP)acac:MEH-PPV | 977 nm |

It should be noted that the light emitted from a TFEL source such as described herein is not generally a pure light at any given wavelength. Rather, the light source produces a spectrum of light that frequently exhibits sharp peaks in intensity at one or more wavelengths. The approximate wavelength of the dominant intensity peaks are listed in the table above for the exemplary dopants listed.

Thin Film Electroluminescent illuminators may be fabricated in sizes ranging from a few millimeters to a few feet on each side with simple two wire connections. Uniform light intensity over the entire illuminator surface area is achieved with uniform dopant distribution and film thicknesses in the TFEL panel, parameters readily controlled during the manufacturing process.

In the phototherapy device 100 of FIG. 1, a variable voltage source 126 supplies AC voltage to the TFEL panel electrodes 116 and 120 to induce emission of light. In this embodiment, the variable voltage source supplies a voltage under control of microprocessor 130. The microcontroller may control any one or more desired parameters of the AC voltage including, but not limited to, voltage level, frequency and modulation characteristics to control the light output from the TFEL panel. The desired output level and other parameters can be controlled by user input to a control panel 134 operating as a user interface providing I/O functions to the microprocessor 130. Such parameters may be directly controlled in some embodiments or controlled as a function of treatment selections made at the control panel without knowledge of the actual physical parameters being influenced.

In the embodiment illustrated, if multiple dopants are used and uniformly distributed, then light is emitted at multiple frequencies at a variable intensity level and time that is controllable by microprocessor 130 which acts as a controller upon appropriate receipt of user input at control panel 134. According to this design, the TFEL source can be manufactured and operated as a single illuminator with the entire panel uniformly activated. One or more conductive elements is attached to both the top and bottom electrode of the TFEL panel and connected to a suitable power source such as source 126. This simple design results in a reliable TFEL illuminator since there are minimal components and minimal connections, and produces a device that is light in weight with low heat generation and low current drain. In this embodiment, all available spectra of light from the TFEL panel are produced whenever an appropriate voltage is applied to the panel. For inorganic TFEL, a relatively high voltage (~200V) may be required to produce light emissions. In this case, the voltage source 126 may incorporate a voltage converter to appropriately boost the voltage to required levels. However, it should be noted that high voltage does not imply limitations on portability since current TFEL flat panel displays are commercially available for battery operated applications with simple input power requirements. In addition, TFEL displays have superb shock resistance and can normally operate at −25° C. to +65° C.

Figure 2:
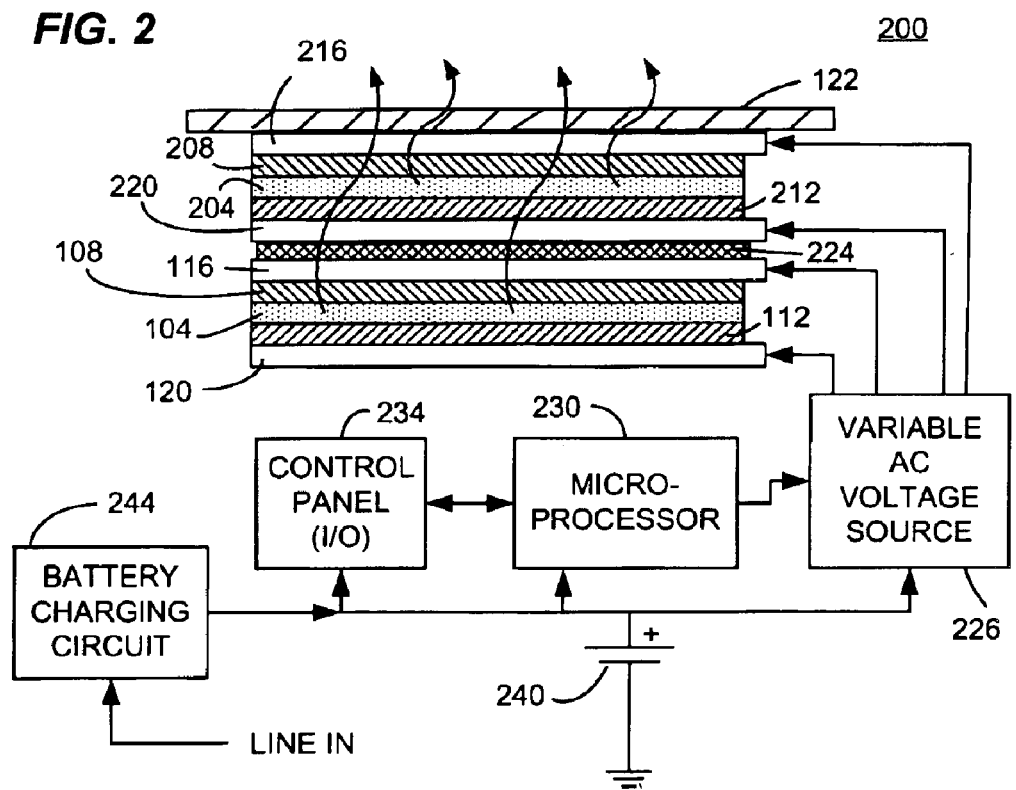
FIG. 2 is a cross sectional view of a thin film electroluminescent light source and associated circuitry consistent with certain embodiments of the present invention.

In an alternative embodiment, illustrated in FIG. 2, a phototherapy device 200 is illustrated in which multiple light spectra are individually selectable. In this embodiment, two (or more) TFEL panels are essentially stacked to provide the user with the ability to individually address each panel and thus select one of two wavelengths (or sets of wavelengths) for the phototherapy treatment protocol. For an inorganic TFEL, the first panel structure is similar to that of FIG. 1 in which the active layer 104, surrounded by insulators 108 and 112 are sandwiched between transparent electrode 116 and electrode 120 (Electrode 120 is preferably reflective at the wavelengths of interest.). A second TFEL panel is fabricated by sandwiching a second active layer 204 between two transparent insulators 208 and 212. This sandwich is in turn sandwiched between a pair of transparent electrodes 216 and 220. Electrode 220 is then coupled to electrode 116 using a transparent insulating glue or tape 224 or other mechanism to hold the two panels together. Note that, in another embodiment, a single electrode could be substituted for electrodes 220 and 116 by appropriate modification of the outputs from the variable voltage source. (In the case of an organic TFEL embodiment, the structural changes discussed in connection with FIG. 1 can be applied equally to the structure of FIG. 2 to achieve a multiple layer organic active layer TFEL.)

In this embodiment, variable voltage source 226 supplies voltage across electrodes 116 and 120 and across electrodes 216 and 220. The device is again isolated from the user's skin by seal layer 122. Thus, the light emission from the top panel and the bottom panel can be independently selected by selective application of voltage to the two stacked TFEL panels. Due to having to pass through the upper TFEL panel, emissions from the lower TFEL panel will be slightly attenuated compared to those from the upper TFEL panel, and this should be accounted for in development of treatment protocols. Since the thickness of each EL panel can be ~1 μm, the attenuation is generally low (~10%). The output, as in device 100, is selected by controlling the variable voltage source 226 by microprocessor 230 operating under control of a computer program with the user input selected via control panel 234. Due to the low current consumption of the TFEL panel, this apparatus (as well as apparatus 100) may be readily battery powered by battery 240. Battery 240 can either be replaceable batteries or may be a rechargeable battery that can be charged by battery charging circuit 244. This circuit may also incorporate voltage regulators and voltage converters (for inorganic TFEL) and other peripheral circuitry as will be clear to those skilled in the art to assure uniformity of voltage, etc.

Figure 3:
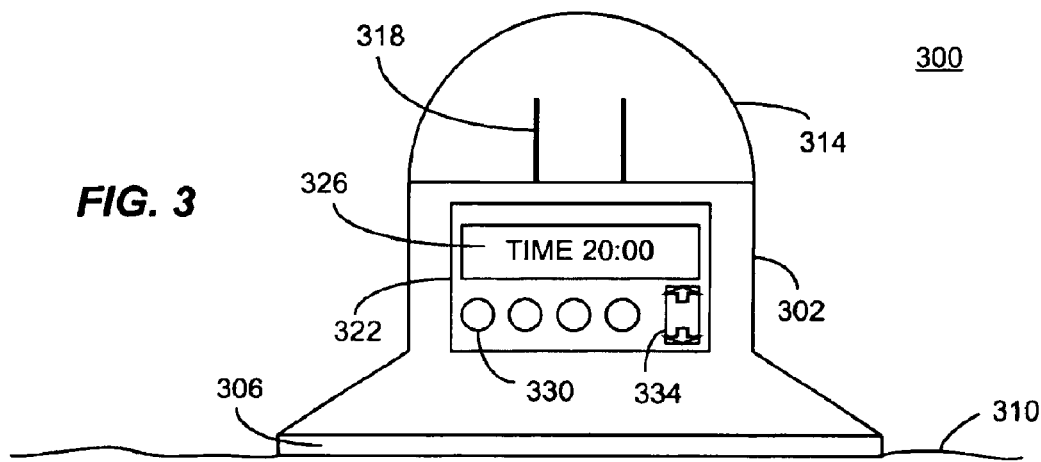
FIG. 3 is an illustration of a hand-held rechargeable thin film EL light source for phototherapy consistent with certain embodiments of the present invention.

In accordance with one embodiment consistent with the present invention, either a stacked or single TFEL panel with the associated circuitry as in devices 100 or 200 can be mounted within a portable housing and used in carrying out phototherapy treatments. One embodiment of such a device is illustrated in FIG. 3 as device 300. In this illustrative embodiment, the circuitry of device 200 is mounted within a housing 302 such that either a single or multiple stacked TFEL panel 306 is exposed as the lower surface thereof. This panel 306 can directly be applied to the skin 310 (or can be held above it if desired) of the patient to impart the desired dosage of light radiation at the desired wavelength to the affected area. Housing 302 of embodiment 300 has a removable top 314 that covers a two or three prong household electrical plug 318 that can be directly plugged into an electrical outlet to charge the battery.

The user interface (e.g., control panel 234) 322 may have a display 326, which is depicted in the form of an LCD or other display (but may be as simple as indicator lights) and input controls such as buttons. In one embodiment, one button such as 330 is provided to indicate entry of each of several parameters (e.g., time, intensity, spectrum or wavelength selection) and one button is used to start or stop a treatment (turn on or off the light in accord with the treatment protocol). Up/down buttons 334 are used to increase or decrease the parameters selected by the buttons. This embodiment should be considered but one illustrative embodiment of a user interface consistent with the present invention with many other suitable interfaces being within the scope of the present invention.

Figure 4:
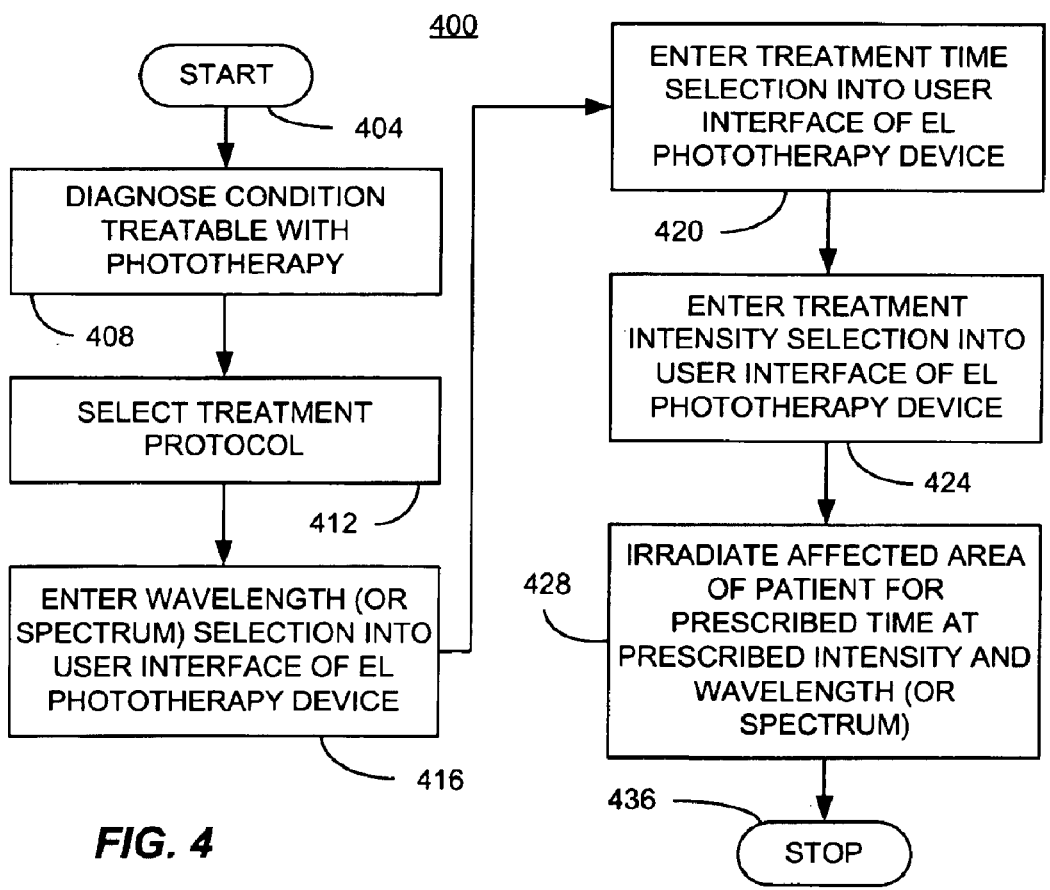
FIG. 4 is a flow chart of a phototherapy process for using a thin film EL light source consistent with certain embodiments of the present invention.

To use the phototherapy device of the present invention, the process 400 illustrated in FIG. 4 can be used starting at 404. When a condition treatable by phototherapy is diagnosed at 408, the user selects a treatment protocol at 412. Using the user interface of the TFEL phototherapy device, the user enters the wavelength or spectrum prescribed by the protocol for specific treatment conditions at 416. The treatment time and intensity are similarly entered at 420 and 424 in the user interface of the TFEL phototherapy device. The affected area is then irradiated with light from the TFEL phototherapy device for the prescribed time, at the prescribed wavelength or spectrum and the prescribed intensity at 428. The treatment ends at 436.

Of course, those skilled in the art will recognize upon consideration of the present teaching, that the entry of time, wavelength or spectrum and intensity can be rearranged without departing from the invention. Moreover, since the intensity of light produced by electroluminescent panels is lower than that produced from other light sources, it may be unnecessary to select an intensity level without departing from the invention. Other variations will occur to those skilled in the art upon consideration of the present teaching including, but not limited to, use of simpler devices having only a single wavelength or spectral output or simplified controls such as a single switch that when actuated produces a fixed time of output, perhaps with multiple actuations multiplying the fixed time (e.g., one actuation=5 minutes, 3 actuations=15 minutes). In still other embodiments, the device can be controlled by connection to an external computer that provides the appropriate interface.

A TFEL illuminator consistent with certain embodiments of the present invention can be used to accomplish phototherapy or photodynamic therapy for a range of disorders or aesthetic conditions by applying light of a selected wavelength or wavelengths to biological tissue. The range of disorders and aesthetic conditions that are potentially treatable using either phototherapy or photodynamic therapy is broad and including, by way of example and not limitation, herpes, psoriasis, acne, skin cancer, hyperbilrubinemia, wrinkles, cellulite, etc. As a result, the optical parameters utilized will depend on the disorder as well as the type and the three-dimensional placement of the tissue, the stage of healing, and the area to be treated. The optical parameters that determine a protocol are intensity, dose, wavelength, illuminator area, frequency and pulse duration. For each disorder or aesthetic condition to be treated, a selected protocol can be defined and stored in a microprocessor then retrieved when treatment is ready to be administered. Thus, in another embodiment of the invention, the control panel can provide a selection of disorders that are to be treated and the user simply selects the disorder in order to accomplish the process described above.

By way of example, and not limitation, an infant patient with hyperbilirubinemia can be treated by exposure to light generated with an electroluminescent panel using a dopant of Thulium (Tm) to produce light at approximately 480 nm in wavelength (which is close to the peak wavelength of 450–460 nm for light absorption by bilirubin, and within the range of 400–500 nm used for treatment by existing technology). The time and intensity can be calibrated from known treatment protocols for treatment of this disorder, and the device's TFEL panel scaled to a size suitable for exposure of large surface areas of the infant's skin to the TFEL panel's radiation. TFEL panels can be readily scaled to any desired size and are thus conducive to use in both small hand held devices such as that depicted in FIG. 3, as well as larger devices that could be used to illuminate a crib or bed to treat a whole human or animal. In one exemplary embodiment, a TFEL device design can provide for interconnections between several individual TFEL devices to produce one mated illuminating source with bigger surface area by connecting smaller devices along their edges. Thus the illuminating surfaces area can be adjusted if bigger patient body area needs to be treated.

Figure 5:
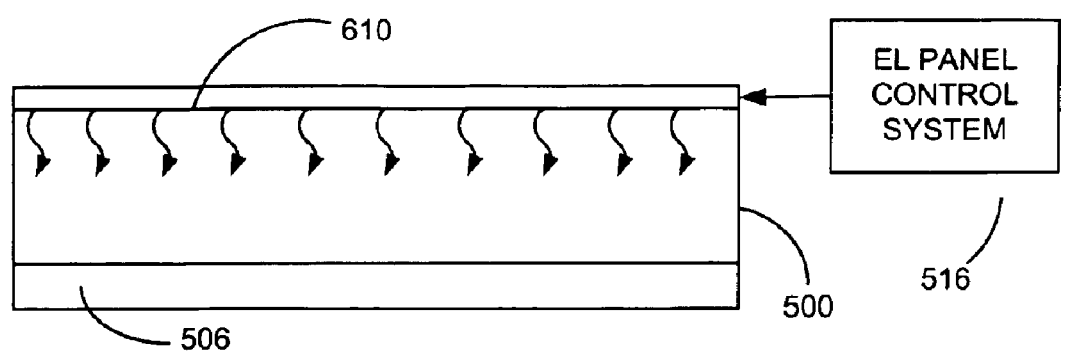
FIG. 5 illustrates a crib or other device for treatment of substantially the whole body of a patient consistent with certain embodiments of the present invention.

One embodiment, consistent with the invention, of a larger structure useful for treatment of an infant, for example, with hyperbilirubenemia is depicted in FIG. 5 as crib 500. Crib 500 has a mattress 506 or other structure to support the patient during treatment. A TFEL panel 510 is suspended above (or otherwise adjacent) the patient so as to substantially irradiate the patient with light. Bias voltage for the TFEL panel 510 is supplied to the panel under control of an electroluminescent panel control system 516. The control system 516 may be similar in design to the control circuitry depicted earlier or the panel may simply entail a power switch that can be used to manually operate the light to provide the patient with a treatment of light from TFEL panel 510.

Figure 6:
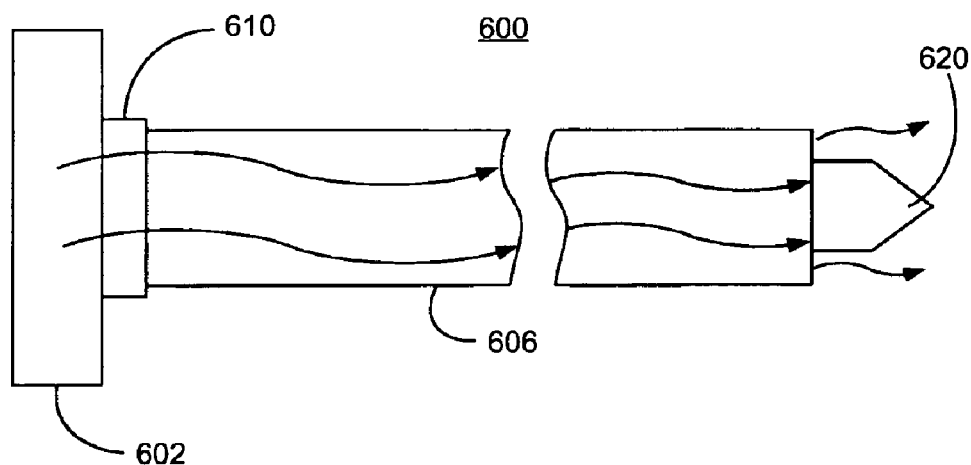
FIG. 6 is a catheter assembly consistent with certain embodiments of the present invention.

In other embodiments of the present invention, it may be desirable to deliver the dosage of light to an area of the patient that can be reached with a catheter. Most commonly, such a catheter might be used to deliver light to a photoreactive substance that has been injected into the patient as a part of a photodynamic therapy regimen in order to condition a portion of the patient's tissue. The substance then reacts with the light in a manner that produces a therapeutic effect. In such cases a catheter arrangement 600 as depicted in FIG. 6 can be utilized in which the electroluminescent panel 602 is coupled to a fiber optic cable 606 (a fiber optic waveguide) using an adhesive or fiber optic connector 610. This permits light to pass from the TFEL panel 602 through the fiber optic cable 606 for delivery to a prescribed location within the patient. The fiber optic cable 606 can be formed as a sleeve around the catheter with the tip 620 of the catheter possibly extending beyond the end of the fiber optic cable.

The phototherapy TFEL panels described above provide a simple structure that is simple to fabricate and provides many advantages over the LED structures currently in use for phototherapy. However, there may be applications wherein a more complex structure may be useful to permit greater flexibility in treatment options. In one such structure, the phosphor may be doped according to a prescribed geometric pattern to permit the user to generate multiple light wavelengths in a substantially uniform manner.

An alternate embodiment involves producing a patterned array of TFEL pixels in order to produce multiple characteristic emission lines. Some of the pixels are designed to emit one wavelength or spectrum while others are designed to produce an alternate wavelength or spectrum by doping the phosphor used to generate the two types of pixels with different dopants. The pixels can be interconnected so that all the pixels of one type can be activated simultaneously. The two, or more, pixel types could be switched on separately to generate emission characteristic of the activated pixels or rapidly switched on and off sequentially producing both types of emission.

Figure 7:
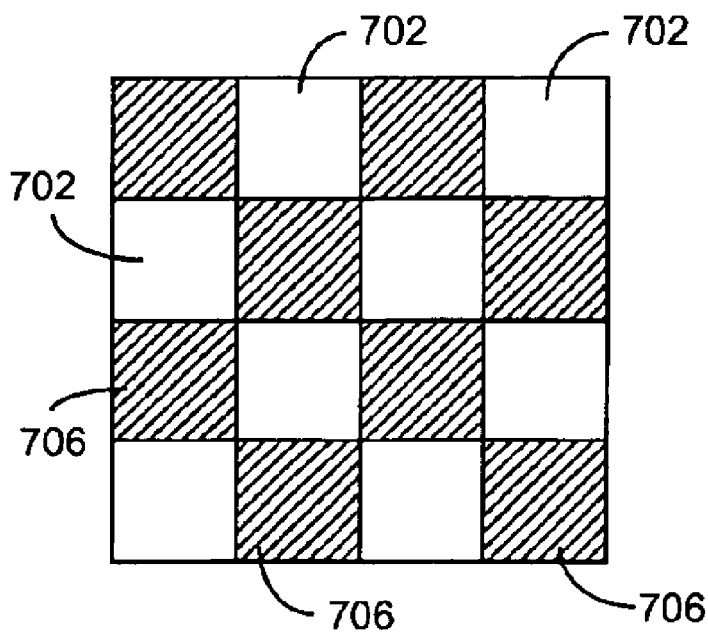
FIG. 7 is an exemplary pixel pattern for a first TFEL panel consistent with certain embodiments of the present invention.

FIG. 7 illustrates one embodiment that uses arrays of pixels in a prescribed pattern to produce multiple spectra of light emissions. In this embodiment, a checkerboard pattern is used with alternating segments of doped electroluminescent material being doped with two different dopants. For example, a first dopant can be used to dope segments 702 (represented by the white squares), while a second dopant can be used to dope segments 706 (represented by the hashed squares) in the same manner used to create pixels in a video display. In a case of organic TFEL based on light emitting polymers which do not require dopants, these segments can be made of different types of light emitting polymers. Electrodes are fabricated so that each of the segments 702 can be collectively addressed (again in a manner similar to that used in video displays, except that all pixels associated with each spectrum can be addressed simultaneously) and each of the segments 706 can be collectively addressed. The user can then address segments 702 with appropriate drive voltage to produce light at the wavelength associated with the dopant used in the segments associated with 702. The user can separately or simultaneously address the segments 706 associated with the second dopant to produce light having different spectral characteristics. As the segments are made smaller and smaller, the light from the panel becomes more uniform, but the panel becomes somewhat more complex and expensive to manufacture. Similarly, depending on applications, TFEL a panel with only one dopant can also be pixilated. The pixel size can range from several mm to several inches.

Figure 8:
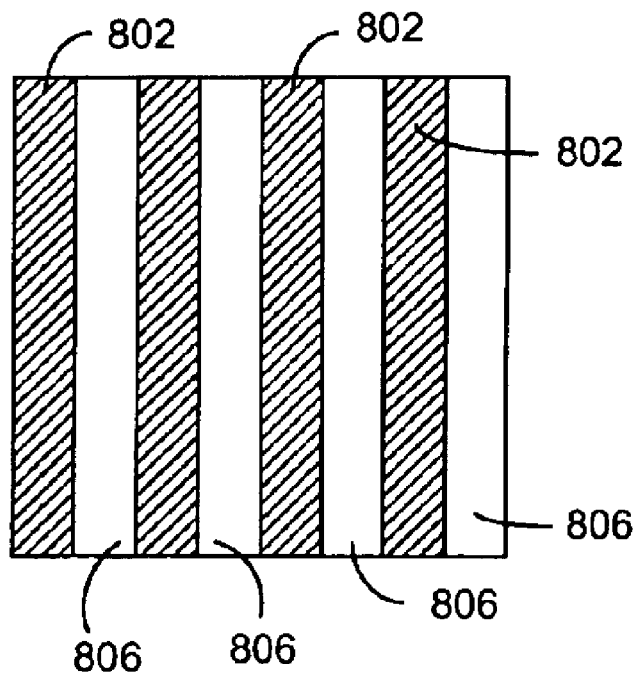
FIG. 8 is an exemplary pixel pattern for a second TFEL panel consistent with certain embodiments of the present invention.

A somewhat simpler structure is illustrated in FIG. 8 in which alternating segments of the panel with first and second dopants are fabricated in successive columns. Thus, a column 802 has the first dopant and the column 806 has the second dopant. Again, the complexity of manufacture increases as the columns are made smaller, but the uniformity of the output becomes better. Of course, those skilled in the art will appreciate upon consideration of this discussion that other arrangements of doped segments of the panel can be devised and that the present invention is not limited to two such dopants. Moreover, multiple dopants can be used for each of the segments of the panel and multiple layers can be used with these embodiments without departing from the present invention.

In addition to the embodiments described in connection with FIGS. 7 and 8, multiple layers (similar to FIG. 2) can be used to generate the pixels with an upper layer contributing to a first spectrum and the lower layer contributing to the second layer with the pixels alternating with one another as in FIG. 7 and FIG. 8 to provide the user with the option of selection of either of the two spectra. Other variations will occur to those skilled in the art upon consideration of the present discussion.

As previously noted, a further aspect of the present invention is the ability to bring the illuminator, the TFEL panel, in direct contact with the skin without the necessity of a cooling device. Other illuminators, such as LEDs exhibit higher power dissipation than TFEL devices. They often produce a significant amount of heat and may require a cooling mechanism. The TFEL illuminator may feel warm when in contact with the skin under normal operating conditions, but does not produce enough heat to require supplemental cooling. The TFEL can be comfortably and safely used for extended periods of time if required.

The exact protocol to be used with any given phototherapy device depends upon a number of parameters including, but not limited to, wavelength output from the device, intensity, time, severity of the affliction being treated, and other parameters. Even devices of similar design can exhibit different output characteristics depending upon slight differences in design. This is evidenced by wide ranges in treatment protocols given in the literature. For example, U.S. Pat. No. 6,063,108 to Salansky et al., which is hereby incorporated by reference, tabulates therapeutic ranges of light wavelengths and intensity for treatment of various afflictions. Many of the afflictions noted in this patent are indicated to be treatable by light in the wavelength range and intensity range that can be produced using a TFEL light source.

As a starting point for estimation of dosing for electroluminescent phototherapy, the output power density of inorganic and organic EL sources is generally in the range of approximately 0.025 $mW/cm^2$ to approximately 0.1 $mW/cm^2$. Current LED technology provides approximately 10–50 $mW/cm^2$ at the head of the LED itself. It is noted, however, LED systems generally incorporate a diffuser that reduces the light output and the distance between the diffuser and the patient is normally kept at approximately 1–2 inches. Thus, although the EL source produces a lower output, the source can be placed in direct contact with the skin reducing the losses generally encountered in the use of LED technology.

Salanski, et al. report data for phototherapy using devices operating in the range of 0.2 $mW/cm^2$ to 100 $mW/cm^2$. As an example of dosing, to produce dosages in the range of 0.05 $J/cm^2$, Salanski et al. can use a 10 $mW/cm^2$ source for 0.0833 minutes. A similar dosing can be achieved using a much lower power density of 0.1 $mW/cm^2$ for a longer duration of 8.33 minutes. Thus, a longer exposure time at a lower power will generally produce a similar dosing. Of course, tests should be performed to assure that an equivalent biological effect can be obtained even though a similar dose is achieved. In this case, a factor of 10 decrease in power density can be compensated by approximately a factor of 10 increase in time. But, in general in order to achieve the therapeutic effect, power density should not be lower than a minimal predetermined power density at a particular wavelength used for treating of a given disorder. This can be determined experimentally for the given TFEL device. It should also be noted that as the technology for generation of light using thin film electroluminescent panels progresses, it can be readily anticipated that the level of light output obtainable will increase and thus reduce the treatment times. It should be possible to similarly adapt dosing from known protocols to EL phototherapy by adjustment of time to compensate for differences in power, since the dose= power density×exposure time.

Thus, a method of carrying out phototherapy, consistent with certain embodiments of the invention, involves diagnosing a medical or aesthetic condition of an affected area of tissue that can be treated with phototherapy determining a treatment protocol for the condition; and irradiating the affected area of tissue with light from an electroluminescent light source in accordance with the treatment protocol. The treatment protocol in such a treatment may specify any number of parameters including, but not limited to, a treatment light wavelength, a treatment modulation of the light, and a treatment light intensity for a treatment time.

EXAMPLE

Treatment Protocol for Treatment of Chronic Wounds

In accordance with one exemplary treatment protocol, an EL light source is believed suitable for phototherapy treatment when the patient has been diagnosed with a chronic wound. A treatment protocol has been established by Salansky et al. and others that specifies that chronic ulcers or wounds can be treated by exposure to light in the range of 600–700 nm at a dosage of 0.05 to 0.2 $J/cm^2$ and power densities from 0.2 to 10 $mW/cm^2$. This can be accomplished with a treatment period of approximately 0.33 minutes using a 10 $mW/cm^2$ source for 0.2 $J/cm^2$ dose. Since an organic TFEL light source using, for example, Erbium or Europium as a dopant can produce a light spectrum in this range, with an intensity of approximately 0.5–1 $mW/cm^2$ exposure of the affected tissue to light from a TFEL light source of this type is believed appropriate to provide a similarly effective phototherapy by adjusting the exposure time to approximately between 3.3 and 6.6 minutes administered on the same basis as the above protocol. Of course, such treatment protocol should be confirmed using appropriate test procedures.

The protocols established by Salansky, et al. and others can thus be translated (as a starting point to be verified by appropriate testing), by determining an equivalent dosage using the power density and frequency achieved by the TFEL device and modifying the time accordingly.

Thus, as described above, a thin film electroluminescent phototherapy device, consistent with certain embodiments of the present invention has a battery and a charging circuit coupled to the battery, so that when connected to a source of current acts to charge the battery. Alternatively, current can be supplied from an AC source without use of a battery. A thin film electroluminescent TFEL panel produces light when voltage from the battery is applied. A processor such as a microprocessor is used to control the application of voltage from the battery to the TFEL panel under control of a control program. A housing is used to contain the battery, the charging circuit and the processor and carry the TFEL panel on an outer surface thereof. In one embodiment, the housing incorporates a removable cover that uncovers a household electrical plug useful for supplying charging current to the charger. In other embodiments, other physical arrangements for EL generation of the light can be used, including, but not limited to bed or crib mounted TFEL panels and catheter embodiments.

In use, a method of carrying out phototherapy, consistent with certain embodiments of the invention involves diagnosing a condition of an affected area of tissue that can be treated with phototherapy. A treatment protocol is determined including, for example, a treatment light intensity, a treatment time, a frequency modulation characteristic and a treatment light wavelength(s) suitable for treating the condition. The affected area is then irradiated with light from the TFEL panel in accord with the treatment protocol. Thus, in accordance with certain embodiments consistent with the present invention, a TFEL panel produces uniform light from a non-point light source without need for an array of point sources.

As previously noted, the areas of phototherapy and photodynamic therapy are undergoing rapid development. Yet, a detailed understanding of the mechanism that produces the beneficial effect has not been achieved in many treatments. Accordingly, the present invention should not be constrained by the theories of the mechanism of operation of PT that have been disclosed herein, nor by the treatment protocols described in the literature.

Those skilled in the art will recognize that the present invention has been described in terms of exemplary embodiments based upon use of a programmed processor. However, the invention should not be so limited, since the present invention could be implemented using hardware component equivalents such as special purpose hardware and/or dedicated processors which are equivalents to the invention as described and claimed. Similarly, general purpose computers, microprocessor based computers, microcontrollers, optical computers, analog computers, dedicated processors, Application Specific Integrated Circuits (ASICs) and/or dedicated hard wired logic may be used to construct alternative equivalent embodiments of the present invention.

Those skilled in the art will appreciate that the program steps and associated data used to implement the embodiments described above can be implemented using any suitable electronic storage medium such as for example disc storage devices, Read Only Memory (ROM) devices, Random Access Memory (RAM) devices; optical storage devices, magnetic storage devices, magneto-optical storage devices, network storage devices, flash memory and/or other equivalent storage technologies without departing from the present invention. Such alternative storage devices should be considered equivalents.

The present invention, as described in embodiments herein, is implemented using a programmed processor executing programming instructions that are broadly described above in flow chart form that can be stored on any suitable electronic storage medium and/or transmitted over any suitable electronic communication medium. However, those skilled in the art will appreciate that the processes described above can be implemented in any number of variations and in many suitable programming languages without departing from the present invention. For example, the order of certain operations carried out can often be varied, additional operations can be added or operations can be deleted without departing from the invention. Error trapping can be added and/or enhanced and variations can be made in user interface and information presentation without departing from the present invention. Such variations are contemplated and considered equivalent.

While the invention has been described in conjunction with specific embodiments, it is evident that many alternatives, modifications, permutations and variations will become apparent to those skilled in the art in light of the foregoing description. Accordingly, it is intended that the present invention embrace all such alternatives, modifications and variations as fall within the scope of the appended claims.

What is claimed is:

1. An electroluminescent phototherapy apparatus, comprising:
   a thin film electroluminescent (TFEL) panel that produces light radiation when a voltage greater than a prescribed voltage is applied thereto;
   the TFEL panel having a light emitting surface that produces light radiation for delivery to a patient; and
   control means, for controlling phototherapeutic parameters for patient exposure to the phototherapeutic light radiation.

2. The phototherapy apparatus according to claim 1, wherein the control means comprises a processor that controls the application of voltage from a voltage source to the TFEL panel under control of a control program.

3. The phototherapy apparatus according to claim 2, wherein the processor further controls a spectral output from the TFEL panel.

4. The phototherapy apparatus according to claim 2, wherein the processor further controls a light power density from the TFEL panel.

5. The phototherapy apparatus according to claim 2, wherein the voltage source comprises a battery.

6. The phototherapy device according to claim 2, further comprising a user interface for entering control information for use by said processor.

7. The phototherapy device according to claim 2, wherein the processor controls at least on of exposure time, light power density, light modulation and light spectrum.

8. The phototherapy apparatus according to claim 1, wherein the TFEL panel comprises a sandwich of electrodes surrounding an active thin film electroluminescent material that produce a light spectrum with at least one wavelength characteristic.

9. The phototherapy apparatus according to claim 8, wherein the active thin film electroluminescent material is doped with a dopant to produce light emissions at a wavelength determined by the dopant.

10. The phototherapy apparatus according to claim 8, wherein the active thin film electroluminescent material is an organic material which is undoped.

11. The phototherapy apparatus according to claim 1, wherein the TFEL panel comprises an inorganic TFEL device having an inorganic active layer that is sandwiched between two insulators and further sandwiched between two conductors, and wherein one of the two conductors is transparent.

12. The phototherapy apparatus according to claim 1, wherein the TFEL panel comprises an organic TFEL device having an organic active layer that is sandwiched between two conductors, and wherein one of the two conductors is transparent, and further having a hole injection layer adjacent the organic active layer.

13. The phototherapy apparatus according to claim 1, wherein the TFEL panel comprises an organic TFEL device having an organic active layer that is sandwiched between two conductors, and wherein one of the two conductors is transparent, and further having an electron injection layer adjacent the organic active layer.

14. The phototherapy apparatus according to claim 1, wherein the TFEL panel comprises an organic TFEL device having an organic active layer that is sandwiched between two conductors, and wherein one of the two conductors is transparent, and further having a hole blocking layer adjacent the organic active layer.

15. The phototherapy apparatus according to claim 1, wherein the TFEL panel comprises an organic TFEL device having an organic active layer that is sandwiched between two conductors, and wherein one of the two conductors is transparent, and further having an electron blocking layer adjacent the organic active layer.

16. The phototherapy apparatus according to claim 1, wherein the TFEL panel comprises an organic TFEL device having an organic active layer that is sandwiched between two conductors, and wherein the organic active layer is doped with a dopant to produce light emissions at a wavelength determined by the dopant.

17. The phototherapy apparatus according to claim 1, further comprising a fiber optic cable coupled to the TFEL panel.

18. The phototherapy apparatus according to claim 17, wherein the fiber optic cable forms part of a catheter.

19. The phototherapy apparatus according to claim 1, further comprising a patient support structure, and wherein the TFEL panel is affixed in proximity to the patient support structure to deliver light to an exposed area of the patient's skin when the patient is supported by the support structure.

20. The phototherapy apparatus according to claim 19, wherein the support structure comprises a crib.

21. The phototherapy apparatus according to claim 1, wherein the control means comprises a switch for manual control of actuation of the TFEL panel.

22. The phototherapy apparatus according to claim 1, wherein the control means stores treatment protocols for a variety of conditions treatable with the phototherapy apparatus.

23. An electroluminescent phototherapy apparatus, comprising:
   a thin film electroluminescent (TFEL) panel having a plurality of electrodes on one surface thereof that are individually addressable to produce light from an addressed segment of the panel when a voltage greater than a prescribed voltage is applied thereto;
   the TFEL panel having an electroluminescent core that is doped using a first dopant in a first segment thereof and doped using a second dopant in a second segment thereof;
   the TFEL panel having a light emitting surface that produces light radiation for delivery to a patient; and
   a controller that addresses the multiple electrodes in order to produce light from the first segment at a first wavelength and from the second segment at a second wavelength; and wherein the controller further controls a phototherapeutic parameter.

24. The electroluminescent phototherapy apparatus according to claim 23, wherein the controller further controls a time that the patient is exposed to the light from at least one of the first and second segments.

25. The electroluminescent phototherapy apparatus according to claim 23, wherein the controller comprises a processor that controls the application of voltage from a voltage source to the TFEL panel under control of a control program.

26. The electroluminescent phototherapy apparatus according to claim 23, having a plurality of segments arranged in a checkerboard pattern with the first and second dopants occupying alternating segments of the checkerboard pattern, so that light at either of the first and second wavelengths can be delivered to the patient in a substantially uniform manner by illuminating segments of the checkerboard pattern corresponding to segments with one of the first and second dopant.

27. The electroluminescent phototherapy apparatus according to claim 23, having a plurality of segments arranged in a checkerboard pattern with the first and second types of electroluminescent materials occupying alternating segments of the checkerboard pattern, so that light at either of the first and second wavelengths can be delivered to the patient in a substantially uniform manner by illuminating segments of the checkerboard pattern corresponding to segments with one of the first and second types of electroluminescent materials.

28. The electroluminescent phototherapy apparatus according to claim 23, having a plurality of segments arranged in a pattern of alternating columns with the first and second dopants occupying alternating columns, so that light at either of the first and second wavelengths can be delivered to the patient in a substantially uniform manner by illuminating columns corresponding to one of the first and second dopant.

29. The electroluminescent phototherapy apparatus according to claim 23, further comprising a user interface for entering control information for use by said controller.

30. The electroluminescent phototherapy apparatus according to claim 23, wherein the processor controls at least one of exposure time, light intensity, light modulation and light spectrum.

31. The electroluminescent phototherapy apparatus according to claim 23, further comprising a fiber optic cable coupled to the TFEL panel.

32. The electroluminescent phototherapy apparatus according to claim 31, wherein the fiber optic cable forms part of a catheter.

33. The electroluminescent phototherapy apparatus according to claim 23, further comprising a patient support structure, and wherein the TFEL panel is affixed in proximity to the patient support structure to deliver light to an exposed area of the patient's skin when the patient is supported by the support structure.

34. The electroluminescent phototherapy apparatus according to claim 33, wherein the support structure comprises a crib.

35. The electroluminescent phototherapy apparatus according to claim 33, wherein the controller stores treatment protocols for a variety of conditions treatable with the phototherapy apparatus.

36. A hand held electroluminescent phototherapy device, comprising:
a battery;
a charging circuit coupled to the battery, so that when connected to a source of current acts to charge said battery;
a thin film electroluminescent (TFEL) panel that produces light when voltage from said battery is applied thereto;
a processor that controls the application of voltage from the battery to the TFEL panel under control of a control program of phototherapeutic parameters;
a housing containing said battery, said charging circuit and said processor therein and carrying said TFEL panel on an outer surface thereof.

37. The hand held electroluminescent phototherapy device according to claim 26, further comprising:
a user interface for entering control information for use by said processor.

38. The hand held electroluminescent phototherapy device according to claim 36, wherein the control information comprises at least one of controls at least on of exposure time, light intensity, light modulation and light spectrum.

39. The hand held electroluminescent phototherapy device according to claim 36, wherein a portion of the light has a wavelength that falls in the infrared spectrum.

40. The hand held electroluminescent phototherapy device according to claim 36, wherein a portion of the light has a wavelength that falls in the visible light spectrum.

41. The hand held electroluminescent phototherapy device according to claim 36, wherein the processor stores treatment protocols for a variety of conditions treatable with the phototherapy apparatus.

42. A method of carrying out phototherapy, comprising:
diagnosing a condition of an affected area of tissue that can be treated with phototherapy;
determining a treatment protocol for the condition; and
irradiating the affected area of tissue with light from a thin film electroluminescent (TFEL) panel in accordance with the treatment protocol.

43. The method according to claim 42, wherein the treatment protocol specifies a treatment light wavelength and a treatment light power density for a treatment time.

44. The method according to claim 42, further comprising selecting a light wavelength from a menu of available wavelengths.

45. The method according to claim 42, wherein a portion of the light has a wavelength that falls in the infrared spectrum.

46. The method according to claim 42, wherein a portion of the light has a wavelength that falls in the visible light spectrum.

47. The method according to claim 42, wherein the determining comprises determining at least one of a light intensity, a light modulation, a treatment time and a treatment light wavelength suitable for treating the condition.

48. The method according to claim 42, further comprising conditioning the tissue irradiated with the light with a photoreactive substance.

49. An electroluminescent phototherapy apparatus, comprising:
a thin film electroluminescent (TFEL) panel that produces light radiation when a voltage greater than a prescribed voltage is applied thereto;
the TFEL panel having a light emitting surface that produces light radiation for delivery to a patient, wherein the TFEL panel comprises a stacked arrangement of TFEL panels;
each TFEL panel in the stack comprising a sandwich of electrodes surrounding an active electroluminescent material;
wherein each of the TEEL panels in the stack has a doped electroluminescent material that doped differently than other TFEL panels in the stack to produce light with differing spectral content at each TFEL panel in the stack; and
control means, for controlling a time that the patient is exposed to the light radiation.

50. An electroluminescent phototherapy apparatus, comprising:
a thin film electroluminescent (TFEL) panel that produces light radiation when a voltage greater than a prescribed voltage is applied thereto;
the TFEL panel having a light emitting surface that produces light radiation for delivery to a patient, wherein the TFEL panel comprises a stacked arrangement of TFEL panels;
each TFEL panel in the stack comprising a sandwich of electrodes surrounding an active electroluminescent material;
wherein each of the TFEL panels in the stack has an electroluminescent material that is different than the electroluminescent material of the other TFEL panels in the stack to produce light with differing spectral content at each TFEL panel in the stack; and
control means, for controlling a time that the patient is exposed to the light radiation.

51. A hand held electroluminescent phototherapy device, comprising:
a battery;
a charging circuit coupled to the battery, so that when connected to a source of current acts to charge said battery;
a thin film electroluminescent (TFEL) panel that produces light when voltage from said battery is applied thereto;
a processor that controls the application of voltage from the battery to the TFEL panel under control of a control program;
a housing containing said battery, said charging circuit and said processor therein and carrying said TFEL panel on an outer surface thereof a removable cover forming a part of said housing;

a power connector connected to said charging circuit for connection of said charging circuit to said source of current; and wherein, removal of said removable cover reveals said power connector.

52. A method of carrying out phototherapy, comprising:

diagnosing a condition of an affected area of tissue that can be treated with phototherapy;

determining a treatment protocol for the condition;

irradiating the affected area of tissue with light from a thin film electroluminescent (TFEL) panel in accordance with the treatment protocol; and wherein the electroluminescent light source is placed in physical contact with the affected area of tissue.

53. An electroluminescent phototherapy apparatus, comprising:

a thin film electroluminescent (TFEL) panel that produces light radiation with peaks in spectral intensity at or above the near infra-red spectrum when a voltage greater than a prescribed voltage is applied thereto;

the TFEL panel having a light emitting surface that produces light radiation for delivery to a patient; and control means, for controlling a time that the patient is exposed to the light radiation.

54. The electroluminescent phototherapy apparatus according to claim 53, wherein the TFEL panel comprises a sandwich of electrodes surrounding an electroluminescent material, and wherein the electroluminescent material is doped with a dopant having a rare earth element as a component of the dopant.

55. An electroluminescent phototherapy apparatus, comprising:

a thin film electroluminescent (TFEL) panel that produces light radiation when a voltage greater than a prescribed voltage is applied thereto;

the TFEL panel having an unpixelated light emitting surface that produces light radiation for delivery to a patient; and control means, for controlling a time that the patient is exposed to the light radiation.

56. A method of carrying out phototherapy, comprising:

diagnosing a condition of an affected area of tissue that can be treated with phototherapy;

determining a treatment protocol for the condition; and irradiating the affected area of tissue with light from a thin film electroluminescent (TFEL) panel in accordance with the treatment protocol, the TFEL panel producing light radiation with peaks in spectral intensity at or above the near infra-red spectrum.

57. The method according to claim 56, wherein the TFEL panel comprises a sandwich of electrodes surrounding an electroluminescent material, and wherein the electroluminescent material is doped with a dopant having a rare earth element as a component of the dopant.

58. A method of carrying out phototherapy, comprising:

diagnosing a condition of an affected area of tissue that can be treated with phototherapy;

determining a treatment protocol for the condition; and irradiating the affected area of tissue with light from an unpixelated thin film electroluminescent (TFEL) panel in accordance with the treatment protocol.

* * * * *

UNITED STATES PATENT AND TRADEMARK OFFICE
CERTIFICATE OF CORRECTION

PATENT NO.        : 6,866,678 B2
APPLICATION NO. : 10/315420
DATED             : March 15, 2005
INVENTOR(S)       : Shenderova et al.

It is certified that error appears in the above-identified patent and that said Letters Patent is hereby corrected as shown below:

On title page, page 1, item (73), replace "Interbational" with --International--

On title page, page 2, item (56), left column, line 48, replace "He-ne" with --He-Ne--

On title page, page 2, item (56), left column , line 52, replace "He-ne" with --He-Ne--

On title page, page 2, item (56), right column, line 31, replace "Near-ir" with --Near-IR--

On title page, page 2, item (56), right column, line 49, replace "Nasa" with --NASA--

On title page, page 3, item (56), left column, line 2, replace "Nm" with --nm--

Column 8, line 55, delete "(e.g. doped silicon based)"

Column 11, line 18, replace "last the" with --the last--

Column 17, line 31, replace "TFEL a" with --a TFEL--

Column 21, line 10, replace "on" with --one--

Column 21, line 15, replace "produce" with --produces--

Column 23, line 38, replace "claim 26" with --claim 36--

Column 23, line 43, delete "comprises at least one of" replace "on" with --one--

Column 24, line 27, replace "TEEL" with --TFEL--

Column 24, line 28, replace "that doped" with --that is doped--

Column 24, line 67, insert "residing" after "panel"

UNITED STATES PATENT AND TRADEMARK OFFICE
CERTIFICATE OF CORRECTION

PATENT NO. : 6,866,678 B2
APPLICATION NO. : 10/315420
DATED : March 15, 2005
INVENTOR(S) : Shenderova et al.

It is certified that error appears in the above-identified patent and that said Letters Patent is hereby corrected as shown below:

Column 24, line 68, insert --;-- at the end of the line.

Signed and Sealed this

Thirty-first Day of July, 2007

JON W. DUDAS
*Director of the United States Patent and Trademark Office*